United States Patent
Hurry et al.

(10) Patent No.: US 9,662,413 B2
(45) Date of Patent: May 30, 2017

(54) SELF-ADHESIVE FRAGRANCED GELS

(71) Applicant: Firmenich SA, Geneva (CH)

(72) Inventors: Simon Hurry, Sunninghill (GB); Jane Summers, West Drayton (GB)

(73) Assignee: FIRMENICH SA, Geneva (CH)

( * ) Notice: Subject to any disclaimer, the term of this patent is extended or adjusted under 35 U.S.C. 154(b) by 141 days.

(21) Appl. No.: 14/175,974

(22) Filed: Feb. 7, 2014

(65) Prior Publication Data

US 2014/0154201 A1 Jun. 5, 2014

Related U.S. Application Data

(62) Division of application No. 13/510,139, filed as application No. PCT/IB2010/055479 on Nov. 29, 2010, now abandoned.

(30) Foreign Application Priority Data

Dec. 2, 2009 (EP) ..................... 09177785

(51) Int. Cl.
*A61L 9/04* (2006.01)
*C11B 9/00* (2006.01)
*A61L 9/012* (2006.01)
*A61L 9/05* (2006.01)

(52) U.S. Cl.
CPC ............... *A61L 9/048* (2013.01); *A61L 9/012* (2013.01); *A61L 9/05* (2013.01); *C11B 9/00* (2013.01)

(58) Field of Classification Search
None
See application file for complete search history.

(56) References Cited

U.S. PATENT DOCUMENTS

| 4,128,507 A | 12/1978 | Mitzner | 512/4 |
| 4,511,552 A | 4/1985 | Cox | 424/14 |
| 5,569,583 A | 10/1996 | Greenberg et al. | 435/5 |
| 5,741,482 A | 4/1998 | Modi | 424/76.3 |
| 6,093,769 A | 7/2000 | Burdick et al. | 524/767 |
| 6,667,286 B1 | 12/2003 | Dettinger et al. | 510/191 |
| 7,138,367 B2 | 11/2006 | Hurry et al. | 512/4 |
| 8,143,205 B2 | 3/2012 | Klinkhammer et al. | 510/238 |
| 2008/0099041 A1 | 5/2008 | Evers et al. | 134/3 |
| 2008/0190457 A1 | 8/2008 | Veltman et al. | 134/22.19 |
| 2009/0215909 A1 | 8/2009 | Wortley et al. | 514/772 |

FOREIGN PATENT DOCUMENTS

| EP | 0 864 637 B1 | 9/1998 |
| EP | 1 325 103 B1 | 7/2003 |
| EP | 1 894 578 A1 | 3/2008 |
| WO | WO 99/66021 A1 | 12/1999 |
| WO | WO 02/26925 A1 | 4/2002 |
| WO | WO 03/075966 A1 | 9/2003 |
| WO | WO 2009/105232 A1 | 8/2009 |
| WO | WO 2009/105233 A1 | 8/2009 |

OTHER PUBLICATIONS

International Search Report and Written Opinion, Appl. No. PCT/IB2010/055479, Mar. 4, 2011.

*Primary Examiner* — Tigabu Kassa

(57) ABSTRACT

A method for dispensing an active volatile in the environment surrounding a surface, which comprises applying to the surface a self-adhering, water-resistant gel composition of at least one active volatile ingredient, silica, and a water-soluble cationic polysaccharide, and diffusing or releasing the volatile ingredient(s) from the gel in an amount sufficient to purify or sanitize the surrounding air, both in a dry condition or in the presence of humidity or water. The gel composition remains adhered to the surface and actively releases the volatile ingredient(s) even after being exposed to repeated water flows over the composition.

18 Claims, 1 Drawing Sheet

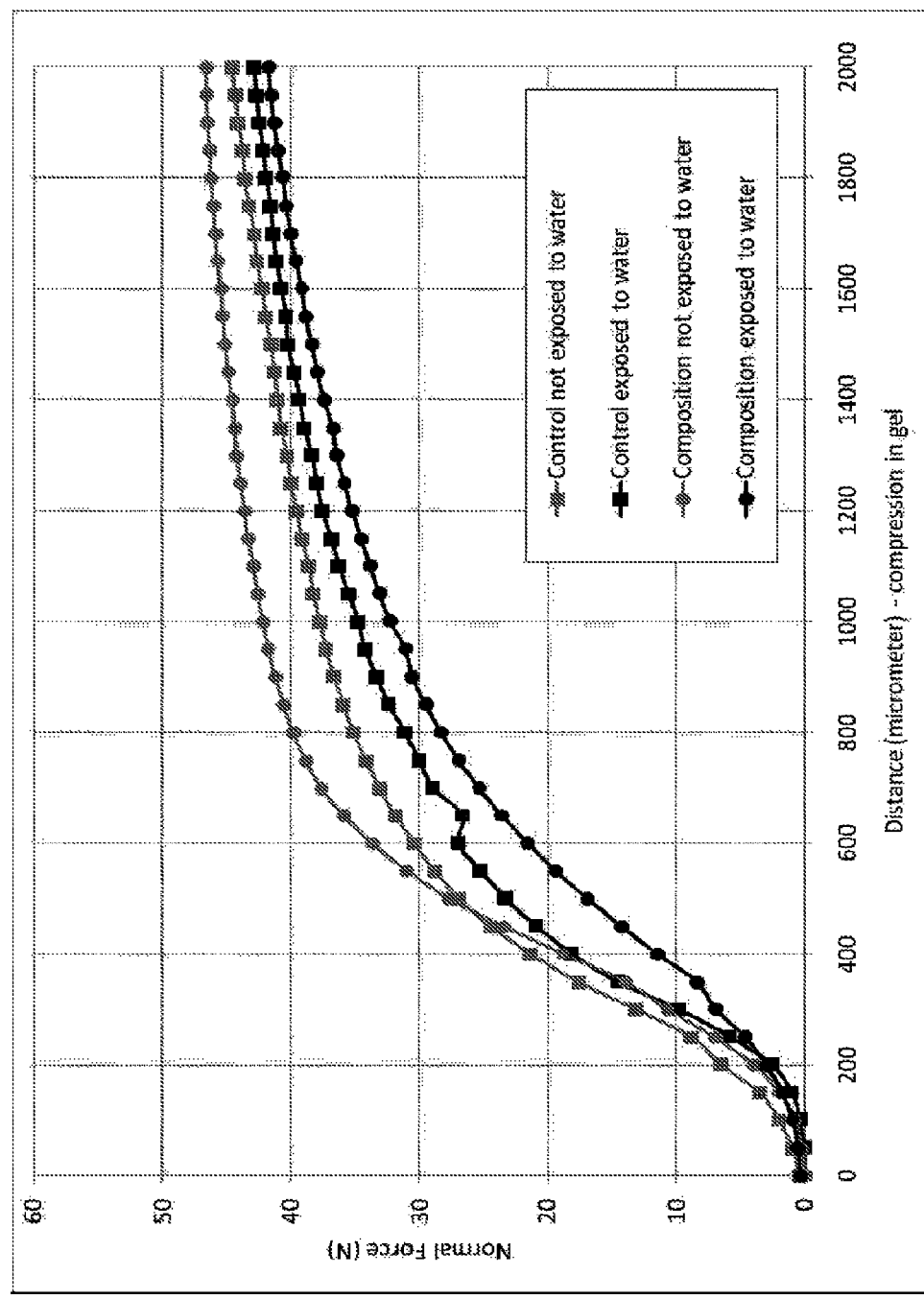

100,0 US 9,662,413 B2

SELF-ADHESIVE FRAGRANCED GELS

CROSS REFERENCE TO RELATED APPLICATIONS

This application is a division of U.S. application Ser. No. 13/510,139 filed May 16, 2012, which is the 371 filing of International patent application no. PCT/IB2010/055479 filed Nov. 29, 2010, which claims priority of European application no. 09177785.4 filed Dec. 2, 2009.

TECHNICAL FIELD

The invention concerns self-adhering, water-resistant gel compositions capable of bringing a benefit or effect into their surrounding environment by diffusing an active volatile substance. The compositions are effective volatile releasing systems in both dry and wet environments and are capable of adhering to a surface to which they are applied. They can be used in a variety of applications, as self-contained fragrance gels or in consumer products.

PRIOR ART

It is known that gel compositions for dispersing volatile materials may be prepared from many different polymeric resins.

However, to the best of our knowledge, no self-adhering, water-resistant gel capable of diffusing an active volatile into its surrounding environment is known from the prior art. The prior known fragranced gels are typically formed of polymeric carriers which require special packaging or other means such as adhesive strips in order to be fixed to the kitchen or bathroom walls or tiles, on which they are typically applied.

Self-adhering gels carrying fragrances have been taught previously in the context of toilet bowl cleaners, in the form of rim blocks for example. However, such rim blocks all have the disadvantage of being able to include only small amounts of volatiles such as perfumes.

Examples of gel compositions useful for the diffusion of volatiles include those taught in WO 03/075966 and U.S. Pat. No. 5,569,583, which both relate to gel compositions used for the diffusion of volatile ingredients, more particularly, perfumes. However, such gels are neither self adhering, nor water-resistant.

Among the known prior art rim blocks, some are self-adhering. For example, WO 2009/105233 relates to self-adhering compositions that may provide residual benefits provided by the composition upon exposure to a layer of water. The rim block described in this document comprises at least one adhesion promoter, at least one surfactant, mineral oil, water and optionally a solvent. It can additionally also comprise a fragrance, in an amount ranging from 0 to 15% by weight, relative to the total weight of the composition.

WO 2009/105232 describes similar compositions, comprising the same maximum amount of fragrance, but preferably comprising not more than 6% by weight of fragrance.

US 2008/0190457 describes a self-sticking cleansing block which disintegrates slowly and releases active ingredients. These compositions comprise 75% to 99% of solid surfactant and 1% to 25% of liquid component. The maximum amount of perfume that can be incorporated in such blocks is of 25% by weight.

U.S. Pat. No. 6,667,286 describes a sanitary agent for cleaning and/or releasing an odorant, comprising an adhesion promoter, water, ionic and/or non-ionic and/or amphoteric surface active agents and, optionally, further common constituents such as odorants, thickeners, colorants and preservatives. However, the odorants may only be present in concentrations ranging from 10 to 25% by weight, relative to the total weight of the composition.

EP 0 864 637 describes gel-based cleansing blocks for lavatory hygiene, with permanent air scenting. The cleansing block is in the form of a lyogel comprising surfactants, flush regulators, gel formers, fragrance and solvents. Again, the amount of perfume that can be incorporated in the lyogel is limited to between 2 and 20% by weight, relative to the total weight of the composition.

EP 1 325 103 describes adhesive sanitary cleaning and deodorizing products comprising water, anionic and/or amphoteric surfactants, an adhesion promoter and at least one additional compound selected from a specific list there-described. It may additionally comprise perfume in an amount of between 1 and 25% by weight, relative to the total weight of the composition.

The present invention does not have as an objective to provide a toilet cleaning composition. The aim of the invention is to provide a concentrated fragrance gel, intended for diffusing fragrance or another volatile of interest to purify or sanitize the surrounding air, both in dry conditions or in the presence of humidity or water. In order to achieve this objective, it is necessary for the gel to be capable of carrying a far larger amount of fragrance than the known rim blocks of the type above-described.

It would therefore be desirable to provide self-adhering, water-resistant gels capable of diffusing high amounts of an active volatile in order to achieve an intense perfuming and/or sanitizing effect. Such gels would be very useful for diffusing perfuming and/or any type of sanitizing vapors for example in a bathroom or in a kitchen, in particular in places where the gel is regularly exposed to a flow of water, as is the case in a shower, wash-basins, sinks, toilets, urinals and the like.

It would be especially useful that the gel washes away slowly and regularly each time water flows over its surface, thus enhancing the release of the active volatile. In particular, gels capable of diffusing the volatile ingredient for a long period would be particularly advantageous, the gel being capable of withstanding an important number of contacts with water without losing its ability to release the volatile ingredient.

The present invention solves the present problem by providing a self adhering gel composition which contains high amounts of volatile ingredients, which are released in both wet and dry conditions, and even when water flows regularly on the gel's surface.

SUMMARY OF THE INVENTION

The invention concerns self-adhering, water resistant gel compositions capable of bringing a benefit or effect into their surrounding environment by diffusing an active volatile substance. The compositions are effective fragrance releasing systems in both dry and wet environments and are capable of adhering to any type of surface, including tiles and other kitchen, bathroom and toilet surfaces, without the need to use additional adhesive or glue means or separate supporting or packaging elements.

As water-resistant gel, it is meant here a gel which is capable of adhering to the surface to which it is applied in the presence of water. It also means that the gel remains active and continues to release volatiles even when exposed to water or humidity and preferably when water flows over the surface of the gel. Preferably, it remains adhered to the surface and active after being exposed at least 40 times, preferably up to at least 100 times, more preferably up to at least 200 times, to a flow of water. However, water resistant does not mean that the gel remains intact on the surface. In particular, it is understood that the gel may preferably wash away and dissolve slowly and gradually when water flows on the surface of the gel. According to a preferred embodiment, the gel is completely dissolved only after being exposed at least 40 times, preferably up to at least 100 times, to a flow of water. According to another preferred embodiment, the exposure to water triggers the release of the active volatile from the gel.

The invention also relates to a method for dispensing an active volatile in the environment surrounding a surface, which comprises applying to the surface a self-adhering, water-resistant gel composition of at least one active volatile ingredient, silica, and a water-soluble cationic polysaccharide, and diffusing or releasing the volatile ingredient(s) from the gel in an amount sufficient to purify or sanitize the surrounding air, both in a dry condition or in the presence of humidity or water. The gel composition remains adhered to the surface and actively releases the volatile ingredient(s) even after being exposed to repeated water flows over the composition.

The self adhering, water resistant gel compositions of the invention comprise:
  between 30 and 95% by weight, relative to the total weight of the gel composition, of an active volatile ingredient or mixture of ingredients;
  silica; and
  a water-soluble cationic polysaccharide.

In a preferred embodiment of the invention, the self adhering, water resistant gel composition may optionally further comprise:
  a mineral filler;
  a solvent;
  water; and/or
  a preservative, an antioxidant and/or an end point indicator.

According to another preferred embodiment of the invention, the composition consists essentially of:
  between 30 and 95% by weight, relative to the total weight of the gel composition, of an active volatile ingredient or mixture of ingredients;
  silica; and
  a water-soluble cationic polysaccharide; and optionally of:
  a mineral filler;
  a solvent;
  water; and/or
  a preservative, an antioxidant and/or an end point indicator.

In a more preferred embodiment, it consists essentially of:
  between 30 and 95% by weight, relative to the total weight of the gel composition, of an active volatile ingredient or mixture of ingredients;
  silica; and
  a water-soluble cationic polysaccharide.

In an even more preferred embodiment, it consists of such ingredients.

In the compositions of any one of the invention's embodiments, the active volatile ingredient or mixture of ingredients is preferably an organic oil capable of bringing a benefit into the surrounding air. Such active volatile ingredient or mixture of ingredients is preferably selected from a perfume, a malodor counteractant, a bactericide, an insecticide, an insect- or animal-repellent or attractant, a sanitizing agent or a mixture thereof. More preferably, it is a perfume and/or a malodor counteractant, most preferably a perfume.

As "perfume" one may use any perfuming ingredient or a mixture thereof. A "perfuming ingredient" is meant here as a compound which is of current use in the perfumery industry, i.e. a compound which is used as active ingredient in perfuming compositions or in perfumed products in order to impart an olfactive and hedonic effect into its surroundings. In other words, such an ingredient or mixture, to be considered as being a perfuming one, must be recognized by a person skilled in the art of perfumery as being able to impart or modify in a positive or pleasant way the odor of a composition, surface, environment or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these perfuming ingredients does not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils. Said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

According to a preferred embodiment, the fragrance has low alcohol content.

By the term "malodor counteractant" or "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Non-limiting examples of suitable insect repellants include citronella, dimethyl phthalate and n,n-dimethyl-m-tolumide.

In yet a more specific embodiment the active ingredient or mixture of ingredients is a perfume or a malodor counteractant.

It is noted that the load of volatile ingredient or mixture of ingredients in the gel compositions of the invention is higher than in any known self-adhering, water-resistant gel. In a preferred embodiment of the invention, the active volatile ingredient or mixture of ingredients is present in an amount ranging from 60 to 95% by weight, relative to the total weight of the composition.

Silica is used as a thickener. For the purpose of any of the invention's embodiments, the silica is preferably fumed silica. Suitable kinds of silica are for example known under the tradename Aerosil® (from Degussa, Germany) or Carbosil® (from Eager Plastics Inc.). The silica provides a high viscosity medium, helping with the gel adherence to surfaces such as tiles and other kitchen, bathroom and toilet surfaces, without the need to use supplementary adhesive or glue means or separate supporting or packaging elements. Silica is preferably comprised in an amount of between 1 and 15% by weight, relative to the total weight of the composition.

The water-soluble cationic polysaccharide used in any of the invention's embodiments is preferably a modified gum. Preferably, the modified gum has a high molecular weight with a low to medium cationic charge density along the chain of the polymer. The cationic charge density is meant here as the number of charges per monomer unit divided by the molecular weight of the monomer unit. Preferably, the cationic charge density is comprised between 0.0001 and 0.002. By a polymer having a "high molecular weight" it is meant here a polymer having a molecular weight comprised between 10000 g/mol and 350000 g/mol. Preferably, the modified gum is an hydroxylated guar gum.

The guar-gums or derivatives thereof are hydrocolloidal polysaccharides which can be obtained from the guar plant. In general, said gums are based on a mannose backbone, and galactose side chains, with a mannose/galactose ratio ranging between 2/1 to 4/1. Suitable derivatives of the guar-gum may be those which have been derivatized with hydroxyalkyl groups which may contain ammonium or sulfonium halide groups. Examples of such derivatizing groups are the following:

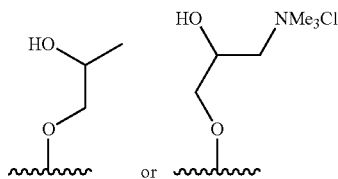

Examples of guar-gums and derivatives thereof which are appropriate for use in any of the gel compositions of the invention are the materials known under the tradename Jaguar® (origin: Rhodia, France).

Preferably, the derivatized guar gum is derivatized with hydroxy $C_2$ to $C_6$ alkyl groups possibly containing a $C_3$ to $C_{20}$ ammonium halide, and the degree of substitution of the polymers being comprised between 0.01 and 1.2. The expression "degree of substitution" refers to the average number of moles of derivatizing groups per anhydro-sugar unit in the gum. An example of such compounds is the one having the CAS Number 39421-75-5, or 2-hydroxypropyl guar-gum ether, also known under the tradename Jaguar®, grade HP 8.

Amongst the above-mentioned derivatized guar-gums, one may cite in particular the ones derivatized with 2-hydroxypropyl-3-(trimethylammoniumchloride) groups and possibly 2-hydroxypropyl groups, the degree of substitution of the polymers being preferably comprised between 0.1 and 0.25. Examples of such compounds are the ones having the CAS Number 65497-29-2, or 2-hydroxypropyl-3-(trimethylammoniumchloride) guar-gum ether, also known under the trademark Jaguar®, grade C-13-S or C 17.

In a preferred embodiment of the invention, the water-soluble cationic polysaccharide, preferably the modified gum as defined in any of the above embodiments, is miscible with the other ingredients at room temperature.

The water-soluble cationic polysaccharide as used in any of the invention's embodiments is preferably present in an amount of from 0.1 to 5%, more preferably from 0.5 to 5%, and even more preferably from 1 to 5% by weight, relative to the total weight of the composition. The higher the concentration of water-soluble cationic polysaccharide, the better the mechanical strength of the composition.

The water-soluble cationic polysaccharide acts as a cross-linking agent, therefore rendering it possible to obtain gel compositions associating an effective release of the active ingredient for a prolonged period of time and good mechanical properties. In particular, the presence of the water-soluble cationic polysaccharide in the compositions of the invention has the advantage of modifying the rheological properties of such composition, as shown in Example 5 below. These modified properties result in the particularly long-lasting self-adherence of the gel to a surface exposed to water and release of fragrance.

The modified gum also has the advantage of being miscible with the other ingredients of the composition at room temperature, so that the gel is formed without heating. This is very advantageous because of the absorption of volatile active ingredient in the gel, part of which would evaporate if the gel was heated during the manufacture process, as is the case with prior known fragrance gels. An additional advantage of said compositions is that they can be produced at room temperature, thus rendering their industrial manufacture advantageous from an energy consumption and equipment point of view.

The combination of the water-soluble cationic polysaccharide and the thickener, as defined above, is essential in order to obtain a suitable gel according to the invention and in particular to obtain a gel having sufficient mechanical strength and adherence to the surface to which it is applied.

The mineral filler is an optional ingredient that can be present in any of the invention's embodiment and can be any mineral solid salt. One particularly useful example of such salts is sodium sulfate. The mineral filler is preferably present in an amount ranging from 0 to 20% by weight, relative to the weight of the composition.

The solvent is also an optional ingredient that can be used in any of the invention's embodiment. Any type of solvent can be used. In particular it can be a solvent of current use in the field of perfumery. Both hydrophilic and hydrophobic solvents can be used. However, hydrophobic solvents are particularly advantageous when the gel composition is used in an environment where it is repeatedly exposed to a flow of water. As examples of suitable solvents, one can cite castor oil and Propylene Glycol Methyl Ether (such as the solvent sold by Dow Chemical under the trade name Dowanol® PM). Preferably, the solvent is present in an amount ranging from 0.1 to 95% by weight, relative to the total weight of the composition.

The invention's compositions may further comprise additional optional components that can have a beneficial effect on the final composition. Said additional optional components may be preservatives, antioxidants or an indicator which helps the consumer to assert when the active volatile is no longer present in the composition, i.e. an end point indicator. The total amount of said optional ingredients may be comprised between 0% and 5%, preferably between 0.01% and 0.5%, the percentage being relative to the weight of the composition.

The compositions of any embodiment of the invention may optionally comprise water. Water has the effect of enhancing the cross-linking of the water-soluble cationic polysaccharide and of further increasing the adherence of the compositions of the invention to various surfaces. Water is preferably present in an amount ranging from 0 to 50% by weight, more preferably from 5 to 15% by weight, relative to the total weight of the composition. When the compositions of the present invention are used in an environment where they are not exposed to water or humidity water, the composition preferably comprises water.

In a preferred embodiment of the invention, the composition of any of the invention's embodiments does not contain any emulsifier. It is also preferably devoid of any cleaning substance.

In another preferred embodiment of the invention, the water-soluble cationic polysaccharide, preferably the modified guar gum as defined in any of the above embodiments, is the only polymer present in the composition. Therefore, the invention's composition is preferably devoid of any polymer other than the water-soluble cationic polysaccharide, as defined in any of the above embodiments.

The compositions of the invention have the advantage of having good mechanical strength and increased adherence on various surfaces. Furthermore, the composition of the invention remains stable in the environment in that it is placed. In particular it is stable when it is in contact with air, in the presence of humidity or when water is repeatedly flowing on the surface on which the composition of the invention is applied.

The compositions of the invention can be used in a variety of applications. In particular they can be used as self-contained volatile releasing gels, preferably fragrance gels, which can for example act as air fresheners, possibly in association with materials, or yet in combination with other elements intended for providing a function other than just the diffusion of the fragrance or perfume.

The compositions of the invention can be used in a volatile material dispenser. Such a volatile material dispenser can be, depending on the nature of the active volatile used in the preparation of the composition, a perfuming or sanitizing device. The volatile material dispenser can be used as an air-freshener of the solid type. It can also be employed as an insecticide or an insect repellent device.

Preferably, it is used for freshening kitchens, bathrooms, toilets, garbage bins or pet litters and more specifically in shower areas, wash-basins, sinks, toilets, urinals, fabric washing machines and the like, where water flows repeatedly. When the device of the present invention is used in a pet litter, the device is preferably exposed to the urine of animals, humidity and/or rain water. Similarly, when the device of the invention is used in garbage bins, such garbage bins are preferably exposed to rain water or humidity.

In another aspect of the invention, the volatile material dispenser consists of the composition of the present invention as such. The composition is applied as such on a surface from which it is intended to diffuse the volatile ingredients into the surrounding medium, which can be either dry or wet.

In another embodiment, the invention provides an air freshener comprising a composition according to any one of the embodiments described above, together with packaging materials.

In a further aspect, the invention provides a method for dispensing an active volatile in the environment surrounding a surface comprising applying a composition of the invention on such surface without the use of adhesive, support or carrying means.

In a preferred embodiment of the invention, the surface is repeatedly exposed to humidity or to a water flow. More preferably such surface is repeatedly exposed to a water flow and most preferably such surface is the wall of a shower, wash-basin, sink, toilets, urinal, fabric washing machine and the like.

In another aspect, the invention relates to a process for preparing self adhering, water resistant gel composition comprising between 30 and 95% by weight of a volatile ingredient or mixture of ingredients, comprising the following steps, which are all carried out at room temperature:

a) mixing the volatile ingredient or mixture of ingredients, optionally pre-mixed with a solvent and/or water, with a water-soluble cationic polysaccharide;

b) optionally adding a mineral filler, a preservative, an antioxidant and/or an end point indicator to the mixture obtained in step a);

c) adding silica to the mixture obtained in step a) or b) under continuous stirring; and d) stirring until complete dispersion of the silica and formation of the self-adhering, water resistant gel composition.

All components used in the process of the present invention are as defined in any of the above embodiments and are preferably used in the concentrations indicated.

Preferably, during the mixing step d), the ingredients are not over-mixed, to avoid breaking down of the gel structure. Stirring is therefore preferably stopped immediately once the silica is completely dispersed and a gel is formed.

EXAMPLES

The invention will now be described in further detail by way of the following examples.

Example 1

Preparation of a Composition According to the Invention

A composition was prepared having to following ingredients.

| Ingredient | Parts by weight [%] |
|---|---|
| Perfume[1] | 33 |
| Sodium Sulfate | 8 |
| Fumed Silica | 8 |
| Castor oil | 50 |
| 2-hydroxypropyl-3-(trimethylammoniumchloride) guar-gum ether[2] | 1 |

[1] Perfume having a pine, balsamic, fruity odor, origin: Firmenich SA, Geneva, Switzerland
[2] Jaguar ® C-13-S, origin: Rhodia Chemicals Ltd.

The perfume was stirred in a beaker with the castor oil. The modified gum was then added and well mixed with the perfume solution. The sodium sulfate was added to this mixture. Fumed silica was then added slowly in small parts under continuous stirring and the mixture was mixed thoroughly during 5 minutes with a spatula until complete dispersion of the silica, to obtain a homogeneous mixture.

Example 2

Preparation of a Composition According to the Invention

A composition was prepared having to following ingredients.

| Ingredient | Parts by weight [%] |
|---|---|
| Perfume[1] | 31 |
| Sodium Sulfate | 8 |
| Fumed Silica | 10 |
| Propylene glycol methyl ether[2] | 50 |
| 2-hydroxypropyl-3-(trimethylammoniumchloride) guar-gum ether[3] | 1 |

[1] Perfume having a pine, balsamic, fruity odor, origin: Firmenich SA, Geneva, Switzerland.
[2] Dowanol ® PM, origin: The Dow Chemical Company.
[3] Jaguar ® C-13-S, origin: Rhodia Chemicals Ltd.

The perfume was stirred in a beaker with the Dowanol® PM. The modified gum was added and mixed well with the perfume solution. The sodium sulfate was then added to this mixture. Fumed silica was finally added slowly in small parts under continuous stirring and the mixture was mixed thoroughly during 5 minutes with a spatula until complete dispersion of the silica, to obtain a homogeneous mixture.

Example 3

Preparation of a Composition According to the Invention

A composition was prepared having to following ingredients.

| Ingredient | Parts by weight [%] |
|---|---|
| Perfume[1] | 33 |
| Sodium Sulfate | 8 |
| Fumed Silica | 8 |
| Castor oil | 40 |
| 2-hydroxypropyl-3-(trimethylammoniumchloride) guar-gum ether[2] | 1 |
| Water | 10 |

[1] Perfume having a pine, balsamic, fruity odor, origin: Firmenich SA, Geneva, Switzerland.
[2] Jaguar ® C-13-S, origin: Rhodia Chemicals Ltd.

The perfume was stirred in a beaker with the castor oil and water. The modified gum was added and well mixed with the perfume solution. The sodium sulfate was then added to this mixture. Fumed silica was finally added slowly in small parts under continuous stirring and the mixture was mixed thoroughly during 5 minutes with a spatula until complete dispersion of the silica, to obtain a homogeneous mixture.

Example 4

Preparation of a Composition According to the Invention

A composition was prepared having to following ingredients.

| Ingredient | Parts by weight [%] |
|---|---|
| Perfume[1] | 83 |
| Sodium Sulfate | 8 |
| Fumed Silica | 8 |
| 2-hydroxypropyl-3-(trimethylammoniumchloride) guar-gum ether[2] | 1 |

[1] Perfume having a pine, balsamic, fruity odor, origin: Firmenich SA, Geneva, Switzerland.
[2] Jaguar ® C-13-S, origin: Rhodia Chemicals Ltd.

The perfume was placed in a beaker. The modified gum was added and well mixed with the perfume. The sodium sulfate was then added to this mixture. Fumed silica was finally added slowly in small parts under continuous stirring and the mixture was mixed thoroughly during 5 minutes with a spatula until complete dispersion of the silica, to obtain a homogeneous mixture.

Example 5

Use of the Compositions According to the Invention

A composition according to the invention and a control were prepared having to following ingredients.

| Ingredient | Amount in Composition [wt. %] | Amount in Control [wt. %] |
|---|---|---|
| Fumed silica | 11.0 | 11.0 |
| Sodium Sulfate | 8.0 | 9.0 |
| Fragrance[1] | 30.0 | 30.0 |
| Castor oil | 50.0 | 50.0 |
| 2-hydroxypropyl-3-(trimethylammoniumchloride) guar-gum ether[2] | 1.0 | — |
| Total | 100.0 | 100.0 |

[1] Perfume having a pine, balsamic, fruity odor, origin: Firmenich SA, Geneva, Switzerland.
[2] Jaguar ® C-13-S, origin: Rhodia Chemicals Ltd.

An amount of 200 g of the Composition and of the Control were prepared. The fumed silica, sodium sulfate and 2-hydroxypropyl-3-(trimethylammoniumchloride) were placed in a Winkworth 'Z' blade mixer and were quickly mixed. The fragrance and castor oil were then poured in. The samples were mixed for five minutes. During mixing, the gel was scraped off from the sides of the mixer chamber occasionally to ensure homogeneous mixing. A gel was formed.

The Composition and the Control were then subjected to a compression test to assess the rheological properties of the gels obtained.

The rheometer used for the testing of the two samples was a stress controlled rheometer AR1000 with the option of the Normal force (located in the peltier). It was used with a Measurement geometry (or compression geometry) Steel Plate with a diameter of 40 mm. The two gels were treated exactly in the same manner and rolled out using a Teflon disc as a guide. The internal diameter of the disc was 60 mm and the height was 8 mm. Therefore the volume of the gel sample can be calculated as being 22.6 cm$^3$. The weight of the tested samples was 25 g.

A compression test was carried out. A gap distance was set to at least 10 000 μm, to put easily the sample gel between the plate and the compression geometry. The sample was then placed on the rheometer, which was started. The compression geometry (steel plate) moves down with a speed of 40 µm/s. Normal force was noted as zero until the plate touched the gel; the gel was then compressed. Measurement of the normal force was plotted as a function of gap distance between the plate and the compression geometry.

The same tests were also carried out for the Composition and the Control after washing with water once placed on the rheometer plate.

FIG. 1 summarizes the results of the rheological test for the Composition and Control, both in dry conditions and after washing of the gel with water. These results show that the increase of the normal force as a function of the gap distance was smaller with the Composition containing the guar-gum than with the Control that did not contain it. It is also evident from the graph that the increase of the normal force was slower for the Composition than for the Control.

The Composition and the Control were also tested for their ability to remain adhered to a surface when exposed to a repeated water flow. An amount of 4 g of the Composition and of the Control, respectively, was rolled into a ball. The experiments were then carried out in temperature and humidity controlled sensory booths. The gel samples were placed in toilet bowls, at the 5 o'clock position. The ball was applied to the bowl by hand, pressing firmly to insure the sample sticks. Flushing was automatically set to every 20 minutes. Each flush uses 8 liters of water.

The samples were monitored visually, and the fragrance performance over time was evaluated.

It was observed that the Composition, containing the guar-gum, became 'sponge' like and initially swelled after flushing, then the mechanical action of the water started to break the sample down and the sample washed away over a long period of time (around 200 flushes). In contrast, the Control without guar-gum washed completely away between 40-60 flushes only.

After 200 flushes the Composition with guar-gum continued to fragrance the booth.

The combined results of both the rheological and performance tests exposed above led to the conclusion that the particular rheological properties of the Composition when it was exposed to water, as highlighted in FIG. 1, were correlated with the surprising long-lastingness of the gel's adherence to the surface and of the fragrance diffusion. Even more surprisingly, FIG. 1 showed that the properties of the Composition of the invention were even improved when the gel was exposed to water, so that the gel was not only water resistant, but its qualities were even enhanced by its exposure to water.

What is claimed is:

1. A method for dispensing an active volatile in the environment surrounding a surface, which comprises applying to the surface a self-adhering, water-resistant gel composition that is free from water or contains less than 15% by weight of water and comprising above 30 up to 95% by weight, relative to the total weight of the gel composition, of at least one active volatile ingredient; silica in an amount of from 1 to 15% by weight of the total weight of the gel composition; and a water-soluble modified guar gum or a hydroxylated guar gum in an amount of from 0.1 to 6% by weight of the total weight of the gel composition to provide strength to the gel; and diffusing or releasing the volatile ingredient(s) from the gel in an amount sufficient to purify or sanitize the surrounding air, both in a dry condition or in the presence of humidity or water; wherein the gel composition remains adhered to the surface while actively releasing the volatile ingredient(s) even after being exposed to repeated water flows over the composition.

2. The method of claim 1, wherein the composition is applied to the surface without the use of adhesives, supports or carrying means but has sufficient adhesiveness such that it adheres to and remains on the surface after at least 100 exposures to a flow of water over the composition.

3. The method of claim 1, wherein a 4 gram sample of the composition applied to the surface is able to diffuse or release the volatile ingredient(s) even after at least 100 exposures to a flow of 8 liters of water over the composition.

4. The method of claim 1, wherein the composition further comprises one or more of a mineral filler; a solvent; a preservative, an antioxidant or an end point indicator.

5. The method of claim 1, wherein the volatile ingredient or mixture of ingredients includes a perfume or a malodor counteractant.

6. The method of claim 1, which further comprises increasing diffusion or releasing of the at least one active volatile ingredient by providing from 60 to 95% of that ingredient in the composition.

7. The method of claim 1 wherein the modified guar gum is present in an amount of from 0.1 to 5%, and comprises guar gum derivatized with hydroxy $C_2$ to $C_6$ alkyl groups optionally containing a $C_3$ to $C_{20}$ ammonium halide.

8. The method of claim 7, wherein the modified gum of the composition is 2-hydroxypropyl-3-(trimethylammoniumchloride) guar-gum ether.

9. The method of claim 1, which further comprises activating the diffusing or releasing of the volatile ingredient(s) from the gel by contacting the gel with water.

10. The method of claim 1, wherein the surface is repeatedly exposed to humidity or to a water flow.

11. The method of claim 1, wherein the surface is in a shower, wash-basin, sink, toilet, urinal, or washing machine, where the surface experiences repeated water flows.

12. The method of claim 1, wherein the surface is part of a volatile material dispenser which diffuses or releases the at least one volatile ingredient, and the ingredient provides perfuming, sanitizing, air-freshening, or is an insecticide or insect repellent.

13. The method of claim 12, wherein the volatile material dispenser is applied in a kitchen, bathroom, garbage bin or pet litter container.

14. The method of claim 12, which further comprises providing the volatile material dispenser as an air freshener together with packaging materials.

15. The method of claim 1, wherein the self-adhering, water resistant gel composition is prepared by the following steps, which are all carried out at room temperature:
  a) mixing the at least one volatile ingredient in amount of above 30 up to 95% by weight, relative to the total weight of the gel composition, optionally pre-mixed with a solvent or with less than 15% by weight of water relative to the total amount of the gel composition or free of water, with a water-soluble modified guar gum or a hydroxylated guar gum in an amount of from 0.1 to 6% by weight of the total weight of the gel composition;
  b) optionally adding a mineral filler, a preservative, an antioxidant and/or an end point indicator to the mixture obtained in step a);
  c) adding silica in an amount of from 1 to 15% by weight of the total weight of the gel composition to the mixture obtained in step a) or b) under continuous stirring; and d) stirring until complete dispersion of the silica and formation of the self-adhering, water resistant gel composition.

16. The method of claim 1, wherein the self-adhering, water resistant gel composition comprises between 60 and 95% by weight, relative to the weight of gel composition, of at least one active volatile ingredient that provides perfuming, sanitizing, air-freshening, or that is an insecticide or insect repellent; silica in an amount of from 1 to 15% by weight; and a water-soluble modified guar gum or a hydroxylated guar gum in an amount of from 0.1 to 5% by weight to provide strength to the gel, with the composition further comprising from 0 to 20% of mineral filler;
from 0 to 95% of solvent;
from 0 to 15% of water; and
from 0 to 5% of a preservative, an antioxidant and/or an end point indicator.

17. The method of claim 16, wherein the modified guar gum comprises guar gum derivatized with hydroxy $C_2$ to $C_6$, alkyl groups optionally containing a $C_3$ to $C_{20}$ ammonium halide.

18. The method of claim 17, wherein the modified gum of the composition is 2-hydroxypropyl-3-(trimethylammoniumchloride) guar-gum ether.

* * * * *

UNITED STATES PATENT AND TRADEMARK OFFICE
CERTIFICATE OF CORRECTION

PATENT NO. : 9,662,413 B2  
APPLICATION NO. : 14/175974  
DATED : May 30, 2017  
INVENTOR(S) : Hurry et al.

Page 1 of 1

It is certified that error appears in the above-identified patent and that said Letters Patent is hereby corrected as shown below:

On the Title Page

Item (72) Inventors, after "Simon Hurry," delete "Sunninghill" and insert -- Ascot --.

In the Claims

Column 12:
Line 23 (Claim 7, Line 1), after "7. The method of claim", delete "1" and insert -- 1, --.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*